US007294697B2

(12) United States Patent
Xu et al.

(10) Patent No.: US 7,294,697 B2
(45) Date of Patent: Nov. 13, 2007

(54) **SHORT CHAIN NEUROTOXIN FROM SEA SNAKE-*LAPEMIS HARDWICKII* AND GENES ENCODING THE NEUROTOXIN**

(75) Inventors: Anlong Xu, Guangzhou (CN); Xiaofen Zhong, Guangzhou (CN); Lisheng Peng, Guangzhou (CN); Jianwen Wei, Guangzhou (CN); Wenyan Wu, Guangzhou (CN); Wenli Yang, Guangzhou (CN)

(73) Assignee: Zhongshan University, Guangzhou (CN)

( * ) Notice: Subject to any disclaimer, the term of this patent is extended or adjusted under 35 U.S.C. 154(b) by 311 days.

(21) Appl. No.: 10/380,734

(22) PCT Filed: Sep. 14, 2001

(86) PCT No.: PCT/CN01/01399

§ 371 (c)(1), (2), (4) Date: Aug. 1, 2003

(87) PCT Pub. No.: WO02/40531

PCT Pub. Date: May 23, 2002

(65) Prior Publication Data

US 2005/0232913 A1 Oct. 20, 2005

(30) Foreign Application Priority Data

Sep. 18, 2000 (CN) ................................ 00 1 24831

(51) Int. Cl.
*C07K 1/00* (2006.01)

(52) U.S. Cl. ......................... 530/350; 530/300; 514/12

(58) Field of Classification Search ..................... None
See application file for complete search history.

(56) References Cited

FOREIGN PATENT DOCUMENTS

WO WO 98/42834 10/1998

OTHER PUBLICATIONS

Zhong et al. (Shengwu Huaxue yu Shengwu Wuli Xuebao, Jul. 2001, vol. 33, No. 4, pp. 457-462).*

"Amino Acid Sequences of the Two Principal Neurotoxins of *Enhydrina schistosa* Venom", L. Fryklund et al., Biochemistry 11 (24), pp. 4633-4640 (1972).

"Amino Acid Sequence of a Snake Neurotoxin from the Venom of *Lapemis hardwickii* and the Detection of a Sulphydryl Group of Laser Raman Spectroscopy", Jay W. Fox et al., Febs Letters, vol. 80 (1), pp. 217-220 (1977).

"Amino Acid Sequence of Pelamitoxin a, The Main Neurotoxin of the Sea Snake, *Pelamis platurus*", C.L. Wang et al., Toxicon vol. 14, pp. 456-466 (1976).

"Hydrophitoxin b from *Hydrophis cyanocinctus* Venom", C.S. Liu et al., Toxicon vol. 12, pp. 543-546 (1974).

* cited by examiner

*Primary Examiner*—Hope Robinson
(74) *Attorney, Agent, or Firm*—Westman, Champlin & Kelly, P.A.; Peter Sawicki

(57) ABSTRACT

In this invention, three genes encoding short chain neurotoxin are obtained by sea snake—*Lapemis hardwickii* venom gland cDNA library construction and DNA sequencing, named sn12, sn36, and sn160, respectively. The three genes are modified and amplified by PCR method, then cloned into expression vector PETTRX. The three neurotoxin genes are all highly expressed in soluble fusion protein in *E. coli* stain BL21-DE3 which is used as a expression host when induced with IPTG. Studies on the analgesic effects of the three recombinant short chain neurotoxins showed that three proteins, SN12, SN36 and SN160 all can significantly increase the pain threshold value of mouse.

2 Claims, 14 Drawing Sheets

Figure 1:
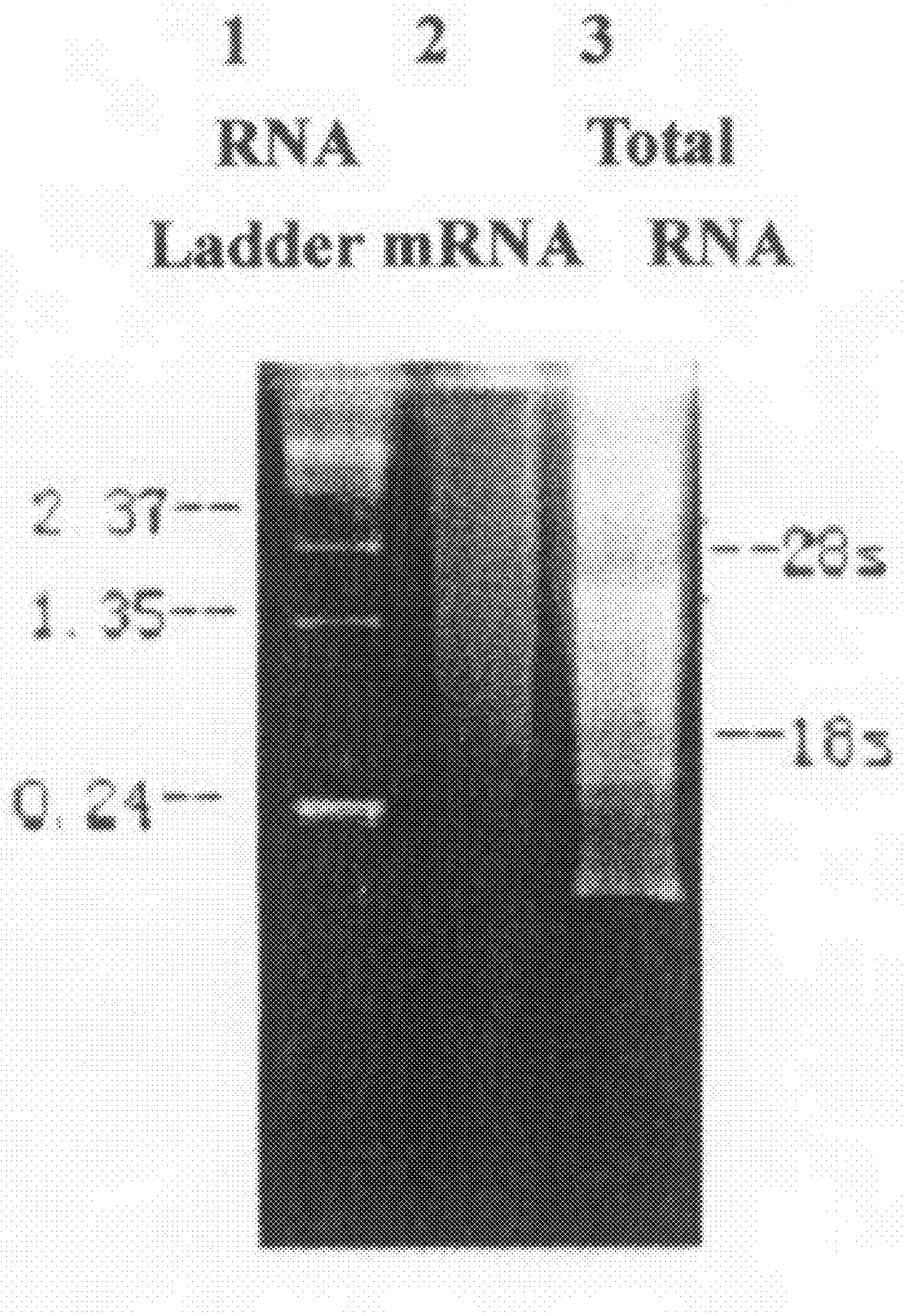

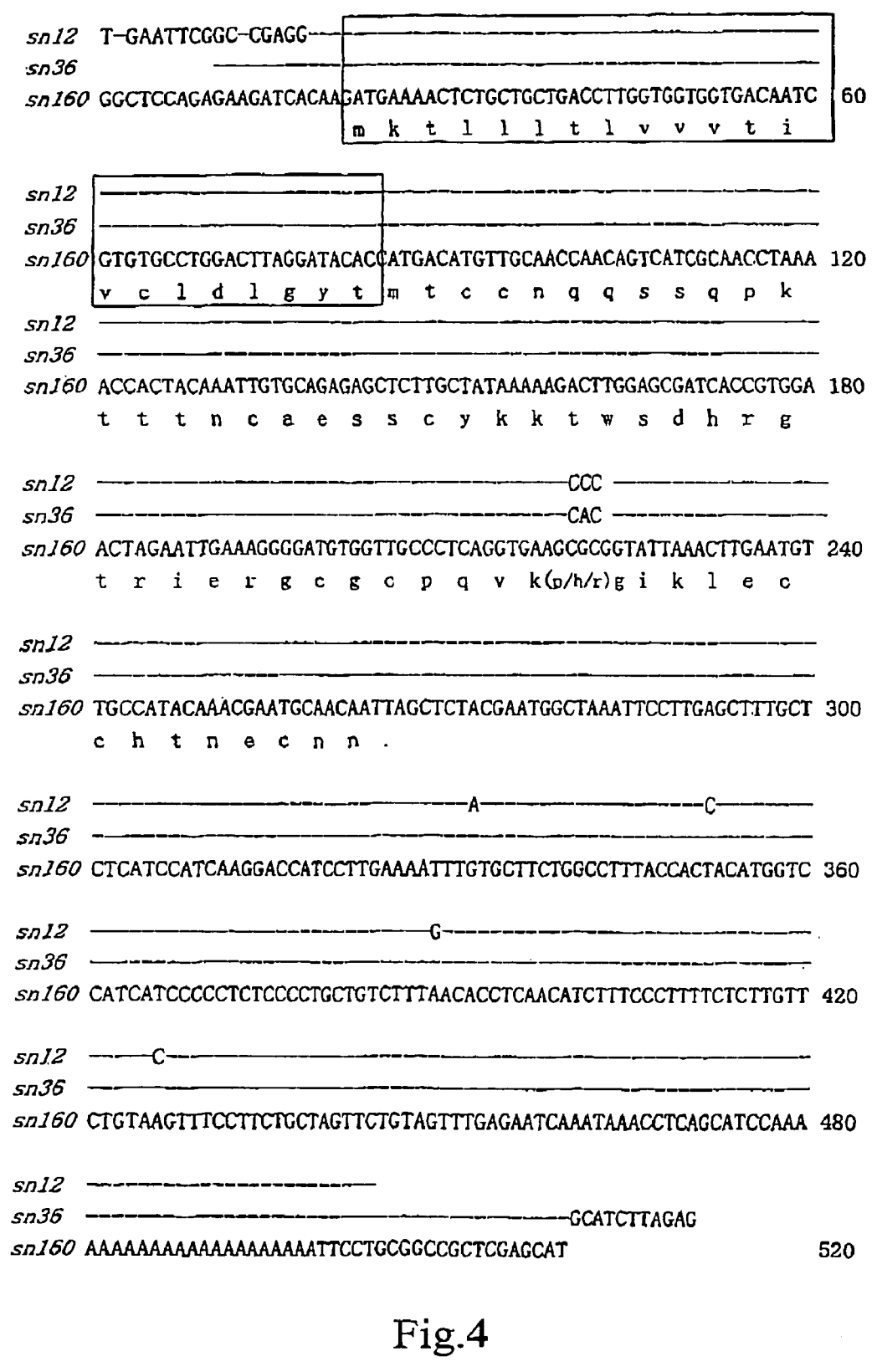

```
sn12  T-GAATTCGGC-CGAGG------------------------------------------
sn36                     --------------------------------------
sn160 GGCTCCAGAGAAGATCACAAGATGAAAACTCTGCTGCTGACCTTGGTGGTGGTGACAATC  60
                          m  k  t  l  l  l  t  l  v  v  v  t  i

sn12  ------------------------------------------------------------
sn36  ------------------------------------------------------------
sn160 GTGTGCCTGGACTTAGGATACACCATGACATGTTGCAACCAACAGTCATCGCAACCTAAA  120
      v  c  l  d  l  g  y  t  m  t  c  c  n  q  q  s  s  q  p  k
sn12  ------------------------------------------------------------
sn36  ------------------------------------------------------------
sn160 ACCACTACAAATTGTGCAGAGAGCTCTTGCTATAAAAAGACTTGGAGCGATCACCGTGGA  180
      t  t  t  n  c  a  e  s  s  c  y  k  k  t  w  s  d  h  r  g

sn12  --------------------------------------CCC-------------------
sn36  --------------------------------------CAC-------------------
sn160 ACTAGAATTGAAAGGGGATGTGGTTGCCCTCAGGTGAAGCGCCGGTATTAAACTTGAATGT  240
      t  r  i  e  r  g  c  g  c  p  q  v  k(p/h/r)g  i  k  l  e  c

sn12  ------------------------------------------------------------
sn36  ------------------------------------------------------------
sn160 TGCCATACAAACGAATGCAACAATTAGCTCTACGAATGGCTAAATTCCTTGAGCTTTGCT  300
      c  h  t  n  e  c  n  n  .

sn12  -------------------------------A-------------------C--------
sn36  ------------------------------------------------------------
sn160 CTCATCCATCAAGGACCATCCTTGAAAATTTGTGCTTCTGGCCTTTACCACTACATGGTC  360

sn12  ----------------------------G-------------------------------
sn36  ------------------------------------------------------------
sn160 CATCATCCCCCTCTCCCCTGCTGTCTTTAACACCTCAACATCTTTCCCTTTTCTCTTGTT  420

sn12  -----C------------------------------------------------------
sn36  ------------------------------------------------------------
sn160 CTGTAAGTTTCCTTCTGCTAGTTCTGTAGTTTGAGAATCAAATAAACCTCAGCATCCAAA  480

sn12  ------------------------
sn36  ----------------------------------------GCATCTTAGAG
sn160 AAAAAAAAAAAAAAAAAAATTCCTGCGGCCGCTCGAGCAT                      520
```

Fig.4

SEQUENCE LISTING

```
<160> NUMBER OF SEQ ID NOS: 4

<210> SEQ ID NO 1
<211> LENGTH: 180
<212> TYPE: DNA
<213> ORGANISM: Lapemis hardwickii
<220> FEATURE:
<221> NAME/KEY: CDS
<222> LOCATION: (1),(180)
<223> OTHER INFORMATION:

<400> SEQUENCE: 1

atg aca tgt tgc aac caa cag tca tcg caa cct aaa acc act aca aat       48
Met Thr Cys Cys Asn Gln Gln Ser Ser Gln Pro Lys Thr Thr Thr Asn
1               5                   10                  15

tgt gca gag agc tct tgc tat aaa aag act tgg agc gat cac cgt gga       96
Cys Ala Glu Ser Ser Cys Tyr Lys Lys Thr Trp Ser Asp His Arg Gly
            20                  25                  30

act aga att gaa agg gga tgt ggt tgc cct cag gtg aag cvc ggt att      144
Thr Arg Ile Glu Arg Gly Cys Gly Cys Pro Gln Val Lys Xaa Gly Ile
        35                  40                  45

aaa ctt gaa tgt tgc cat aca aac gaa tgc aac aat                      180
Lys Leu Glu Cys Cys His Thr Asn Glu Cys Asn Asn
    50                  55                  60


<210> SEQ ID NO 2
<211> LENGTH: 60
<212> TYPE: PRT
<213> ORGANISM: Lapemis hardwickii
<220> FEATURE:
<221> NAME/KEY: misc_feature
<222> LOCATION: (46),(46)
<223> OTHER INFORMATION: Xaa located at position 46 represents His, Arg,
      or Pro

<400> SEQUENCE: 2
```

-continued

```
Met Thr Cys Cys Asn Gln Gln Ser Ser Gln Pro Lys Thr Thr Thr Asn
1               5                   10                  15

Cys Ala Glu Ser Ser Cys Tyr Lys Lys Thr Trp Ser Asp His Arg Gly
            20                  25                  30

Thr Arg Ile Glu Arg Gly Cys Gly Cys Pro Gln Val Lys Xaa Gly Ile
        35                  40                  45

Lys Leu Glu Cys Cys His Thr Asn Glu Cys Asn Asn
    50                  55                  60


<210> SEQ ID NO 3
<211> LENGTH: 47
<212> TYPE: DNA
<213> ORGANISM: Artificial Sequence
<220> FEATURE:
<223> OTHER INFORMATION: primer

<400> SEQUENCE: 3

cggggtaccg acgacgacga taaaatgaca tgttgcaacc aacagtc                   47


<210> SEQ ID NO 4
<211> LENGTH: 35
<212> TYPE: DNA
<213> ORGANISM: Artificial Sequence
<220> FEATURE:
<223> OTHER INFORMATION: primer

<400> SEQUENCE: 4

cgcggatcct taattgttgc attcgtttgt atggc                                35
```

SHORT CHAIN NEUROTOXIN FROM SEA SNAKE-*LAPEMIS HARDWICKII* AND GENES ENCODING THE NEUROTOXIN

CROSS-REFERENCE TO RELATED APPLICATIONS

This application is a 371 of PCT/CN01/01399 filed on Sep. 14, 2001 which claims foreign priority to China 00124831.6, filed Sep. 18, 2000.

STATEMENT REGARDING FEDERALLY SPONSORED RESEARCH OR DEVELOPMENT

Not applicable.

THE NAMES OF THE PARTIES TO A JOINT RESEARCH AGREEMENT

Not applicable.

INCORPORATION-BY-REFERENCE OF MATERIAL SUBMITTED ON A COMPACT DISC

Not Applicable.

BACKGROUND OF THE INVENTION

1. Field of the Invention

The present invention relates to short chain neurotoxins from *Lapemis hardwickii* and their encoding genes.

2. Description of Related Art

Snake neurotoxins are important components of snake venom, widely existing in elapidae and sea snakes. According to their different binding targets, snake neurotoxins can be divided into two main types: presynaptic and postsynaptic neurotoxins (Singh, B. R., Tu, A. T. Overview of snake venom, In: Natural Toxin 2: Structure, Mechanism of Action and Detection. New York: Plenum Press, 1996, 391: 37~62). Presynaptic neurotoxins inhibit acetylcholine release from presynaptic motor nerve ending, and Postsynaptic neurotoxins block nerve conduction by specifically binding to acetylcholine receptors of nicotinic amide type on postsynaptic membrane motor end-plates from vertebrates muscle or electric organs from fishes, thus influence subsequent physiological processes associated with acetylcholine of nicotinic amide type binding to motor end-plates of muscle cells (Toru, T., Satoshi, O., Eisaku, N., et al. Complete nucleotide sequences of cDNAs encoding long chain α-neurotoxins from sea krait, *Laticauda semifasciata. Toxicon.* 1999, 37: 181~185; Qin, G. P. China poisonous snake research: 2$^{nd}$ edition. Guangxi science and technology press. 1998, 372~385). On the basis of molecular weight and the number of inter-chain disulfide bonds, postsynaptic neurotoxins can be subdivided into two groups: short chain and long chain neurotoxins. The former consist of 60 to 62 amino acid residues with four pairs inter-chain disulfide bonds whereas the latter have 66 to 79 amino acid residues with five pairs inter-chain disulfide bonds. The two groups share a common structure characteristic of three-finger loops (Louis, W. C., Robert, S. D. Handbook of Neurotoxicology, New York: Marcel Dekker Inc, 1995, 637~665.).

The predominant clinical features of neurotoxic symptom arise from postsynaptic neurotoxins include: flaccid muscle paralysis in one hour or even sooner, dyspraxia followed by dyspnea, ultimately leading to asphyxiant convulsive death. Artificial breathing may help delay death. Some may even get saved.

Postsynaptic neurotoxins are widely used in the realm of biology and medicine, and of especial importance when applied to molecular biology and molecular pharmacology. Analgesics made from snake neurotoxins can be used to treat rheumatic arthralgia, trifacial neuralgia, sciatica, intercostal neuralgia, swelling pain of late cancer, leprotic neuralgia and so on. The advantages thereof are manifested in rapid and effective analgesia, no tolerance after successive medication, no addiction, low dosage, generally no serious toxic side-effect. Noticeable, its application to the treatment of swelling pain from late cancer is of great significance (Chen, R. Z., et al. Analgesia of cobrotoxin. China pharmacology bulletin. 1998, 4(2): 113~117; Hao, W. X., Chen, Y. C edited. Biochemistry, toxicology and application of snake venom. Science Press: Beijing. 1980, 109~115.). Binding to acetylcholine receptor of nicotinic amide type with high affinity and specificity, postsynaptic neurotoxins may be used to study on neuroreceptors. Some of its application are as follows: a label to detect acetylcholine receptor of nicotinic amide type; to help purify acetylcholine receptor of nicotinic amide type; a tool to study interaction between drugs and receptors; a tool to help investigate the structure and character of acetylcholine receptor of nicotinic amide type. In addition, postsynaptic neurotoxins are especially useful with regard to study on myasthenia gravis. The main clinical symptom of myasthenia gravis is lassitude of striated muscle at slight motion, results from destruction of acetylcholine receptor of nicotinic amide type by autoimmunity. So far, a method of radioactive-iodine labeled neurotoxin and acetylcholine receptor of nicotinic amide type has been employed to test the content of antibody against acetylcholine receptor in patient's serum so as to diagnose the disease. To further study its pathogenic mechanism, short chain neurotoxins are also used to purify subunits of acetylcholine receptor of nicotinic amide type and prepare monoclonal antibody against receptor subunits. This monoclonal antibody can be used to neutralize acetylcholine receptor in animals to probe into a new therapy pathway (China poisonous snake research Qin, G. P. edited: 2$^{nd}$ edition. Guangxi science and technology press. 1998, 495~497).

Production of snake neurotoxin by genetic engineering hold brilliant future, considering the fact that at present snake neurotoxins are mainly obtained by biochemical extraction from snake venom with high cost and low purity. Since the year of 1995 when the gene encoding toxic protein of *Dendroaspis angusticeps* was cloned and expressed (Leonard, A. S., Mark, A. O., Pierre, J. L., et al. Cloning and expression of mamba toxins. *Toxicon,* 1995, 33(4):439~474.), many reports have come out about the production of snake neurotoxins or other toxic polypeptides by biological engineering (Fatemeh, A., Arunmozhiarasi, A., Nget, H. T., et al. Four new postsynaptic neurotoxins from *Naja Naja Sputatrix* venom: cDNA cloning, protein expression, and phylogenetic analysis. *Toxincon.* 1998, 36(12): 1871~1885; Nanling, G., Arunmozhiarasi, A. and Kandiah, J. Postsynaptic short-chain neurotoxins from *Pseudomaja texilis* cDNA cloning, expression and protein characterization. *Eur. J. Biochem.* 1999, 265: 982~989.).

Sea snakes are widely distributed in the warmer drainage area of the Indian Ocean and the Pacific Ocean, and the majority live along the coast of South Asia and East Indian Ocean. They are easily recognized for their level and oar-shaped tail. Sea snake venoms, with exception of that from *Emydocephalus annulatus*, are highly toxic and even more intense than those from land snakes. Yet compositions of sea snake venoms are more simple than those of land snakes (Chikahisa Takasaki, 1998, The Toxinology of Sea Snake Venoms, J. Toxicol.—Toxin Reviews, 17(3): 361~372.). Snake venom neurotoxin is the most toxic component of sea snake venom, which may lead to flaccid paralysis and respiratory failure, and consequently lead to death. Studies on sea snake toxin are much less than those of land snakes at home and abroad. Most of them rest on the protein level. Not many studies are reported on genes encoding sea snake toxins. Up to now, about over 100 amide acid sequences of sea snake toxins have been reported in Genbank whereas no more than 50 nucleotide sequences encoding sea snake toxins can be found.

Because of the intense toxicity and trace expelling, it is difficult to acquire sufficient venom from sea snakes. Thus some difficulties may arise in isolation and purification of compositions of sea snake venom, studies on structure and characterization of toxin and enzyme molecules, as well as in research and application (Marine life toxin research. Song, J. J., Mao, Q. W. edited. Beijing science and technology press: Beijing. 1996, 337~354).

With rapid progress of research on native toxins, the clinical applications have been widely made, considering the highly specific bioactivity that native toxins possess, snake venom obviously takes a predominant position as to the application of toxin. Scientists try to utilize native bioactive substance as an important guide looking for new drugs. The utilization of snake venom has drawn close attention from researchers on pharmacology, medicament, biochemistry and medicine and gained rapid development in the application field. Neurotoxins are mainly found in venoms of snakes belonging to the sea snake family and elapidae, and have a long history of application to analgesia. The first relevant report was from Macht in 1936. Steinbrocker utilized cobrotoxin to treat 65 patients with arthritis or neuralgia in 1940 and got an effective rate up to 59%. The three companies Hynson, Westco and Dunning took advantage of snake venom to produce two analgesics Cobroxin and Nyloxin. The former is neurotoxin, with 1.0 ml per ampule and 50×106 IU in content, directed against intractable pain and carcinoma pain. The latter, with 3.3×106 IU of neurotoxin added by 1.5 ml of silicic acid and 3.3 ml of formic acid to form physiological saline, is targeted at arthralgia. These two drugs are on list of American Bureau of Drug. In 1975, Kunming Zoology Institute of China Science Academy successfully developed cobrotoxin injection using cobrotoxin. The injection has been put to batch manufacture by Wuzhou Pharmaceutical Factory in Guangxi province, commercially designated as “Ketongning Injection”. It is one novel analgesic, characteristic of rapid and effective analgesia, no tolerance after successive medication, no addiction, low dosage and no serious side-effect. It can be used to treat rheumatic arthralgia, trifacial neuralgia, sciatica, intercostal neuralgia, swelling pain of late cancer, leprotic neuralgia and so on. But the drug is restricted to intramuscular injection and it will take 3 to 5 days to take effect accompanied with sclerotic swelling at injection site. Subsequently, snake venom clinical application research center of PLA employed modern techniques to isolate and purify cobrotoxin and prepared one new analgesic named “New Ketongning” which takes effect immediately by either intravenous or intramuscular injection. Cobrotoxin has been used to relieve carcinoma pain, various neuralgia, arthralgia for over 60 years at home and abroad (Chen, R. Z., Wu, X. R. Analgesia of cobrotoxin. China pharmacology bulletin. 1988, Vol: 4, Issue: 2). Cobrotoxin is applied to clinical treatment in many internal hospitals by intravenous or intramuscular injection, and prove to be safe in a dosage of $\frac{1}{2500}^{th}$ of $LD_{50}$ of mice {one dosage each day, 1~2 bottle each time, for particular two dosages each day and 1 bottle each time. As for acute pain, withdrawal on abolition of pain. As for chronic pain, 3~5 more administrations for consolidation. 20 days for one period of treatment and repetitive periods are needed if necessary (Ketongning, 2 ml per bottle with 70 μg neurotoxin)}, safe and reliable (Wang, X. Y/207 hospital, Siping City, Jilin Province., Wang, F. X/chief hospital of battalion, Shenyang, Analgesia observation of New Ketongning after operation. Snake record. 1999, Vol: 11, Issue: 1; Gao, Z. E/traditional Chinese medical hospital, Suhzhou City, Jiangsu Province, Analysis of 182 sciatica treatments with Ketongning matched with traditional Chinese medicine. Snake record. 1998, Vol: 10, Issue: 3; Cao, Y. S., Cheng, B. Q., Zhao, G. H., et al/Military Medical Institute of logistic administration, battalion in Guangzhou/$6^{th}$ people hospital, Guangzhou City., Comparation and observation of clinical analgesia of Ketongning and its compound. China Journal of biochemical drugs. 1996.) Snake neurotoxins are also applied to abstinence of drugs and obtained good treatment effect by oral administration clinically (Yang, L., Li, H., Wu, Y. W et al/treatment centre of studying on drug dependency, Kunming medical college., Clinical effect observation of snake venom capsule in treatment of Heroin addiction. Withdrawal medicine.).

Snake neurotoxins share considerable amide acid sequence homology. At present, available neurotoxins mainly come from snake venom by biochemical extraction which underlie some defects such as high cost and low purity which may always lead to medical negligence. Now snake neurotoxins produced by gene engineering technique not only can solve the above problems, but also have the same effect of medicine comparable with that of native snake neurotoxin.

BRIEF SUMMARY OF THE INVENTION

In this invention, three genes encoding short chain neurotoxin are obtained by sea snake—*Lapemis hardwickii* venom gland cDNA library construction and DNA sequencing, named sn12, sn36, and sn160, respectively. The three genes are modified and amplified by PCR method, then cloned into expression vector PETTRX. The three neurotoxin genes are all highly expressed in soluble fusion protein in *E. coli* stain BL21-DE3 which is used as an expression host when induced with IPTG. Studies on the analgesic effects of the three recombinant short chain neurotoxins showed that three proteins, SN12, SN36 and SN160 all can significantly increase the pain threshold value of mouse.

BRIEF DESCRIPTION OF THE SEVERAL VIEWS OF THE DRAWING(S)

FIG. 1 The electrophoresis result of total RNA and mRNA of sea snake venom glands from *Lapemis hardwickii.*

Figure 2:
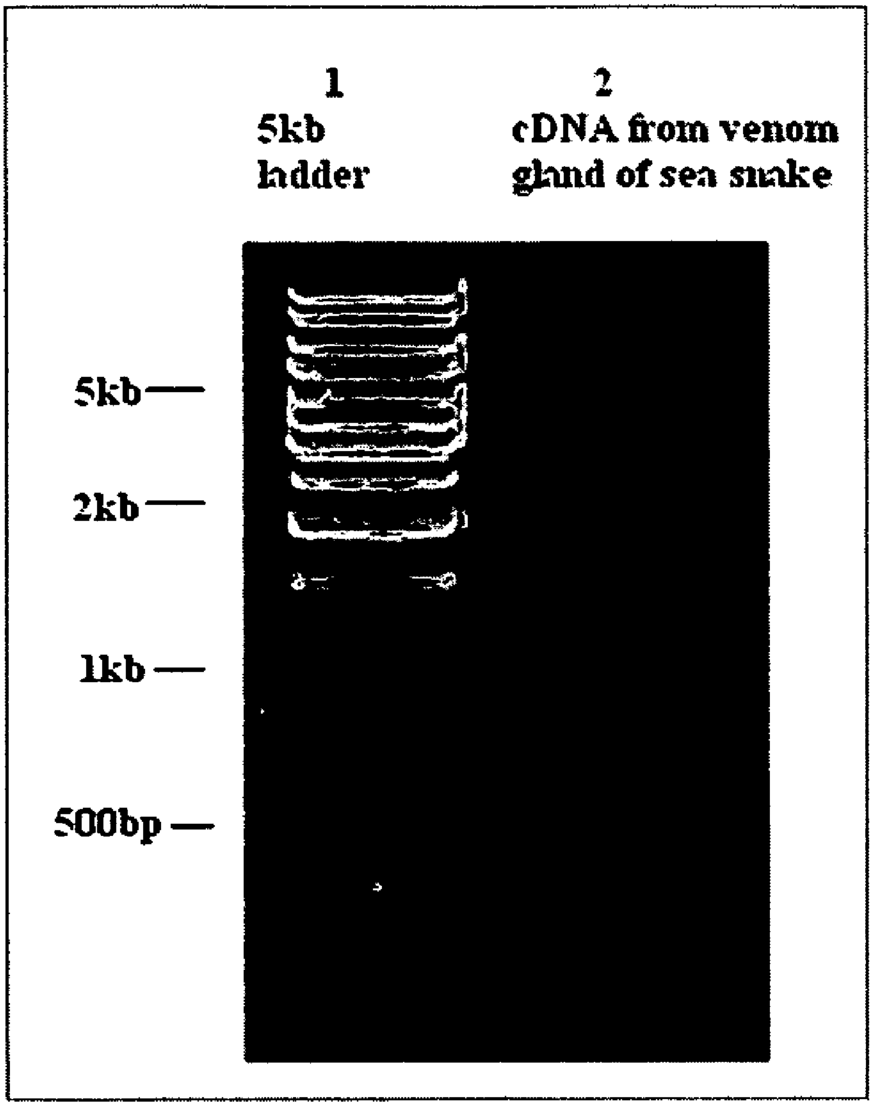

FIG. 2 The electrophoresis result of synthesized cDNA of sea snake venom glands from *Lapemis hardwickii.*

Figure 3:
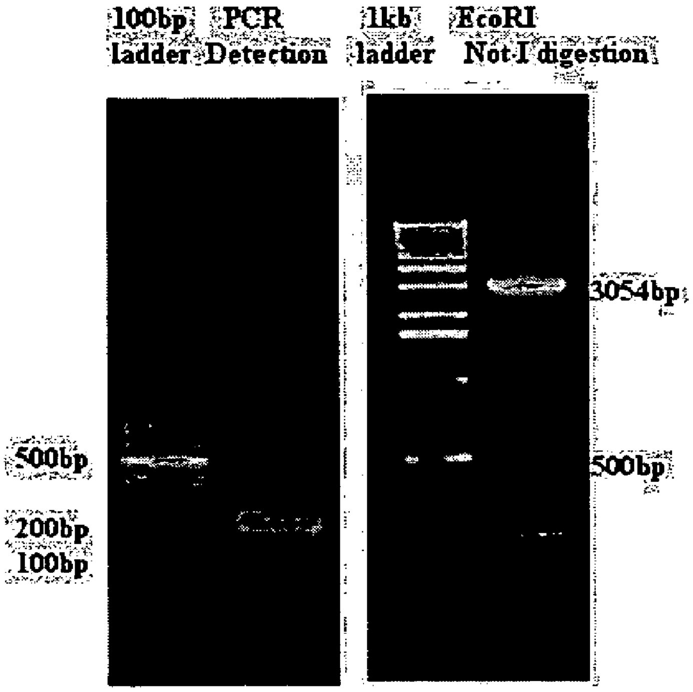

FIG. 3 The electrophoresis result of restriction endonuclease reaction and PCR amplification of the plasmids extracted from the cDNA expressional library of the venom glands from *Lapemis hardwickii.*

FIG. 4 Nucleotide sequences of sn 12 (SEQ ID NO. 5), sn36 (SEQ ID NO.6), and sn160 (SEQ ID NO. 7) and deduced amino acid sequences of sn12 (SEQ ID NO.8), sn36 (SEQ ID NO. 9) and sn160 (SEQ. ID NO. 10).

Figure 5:
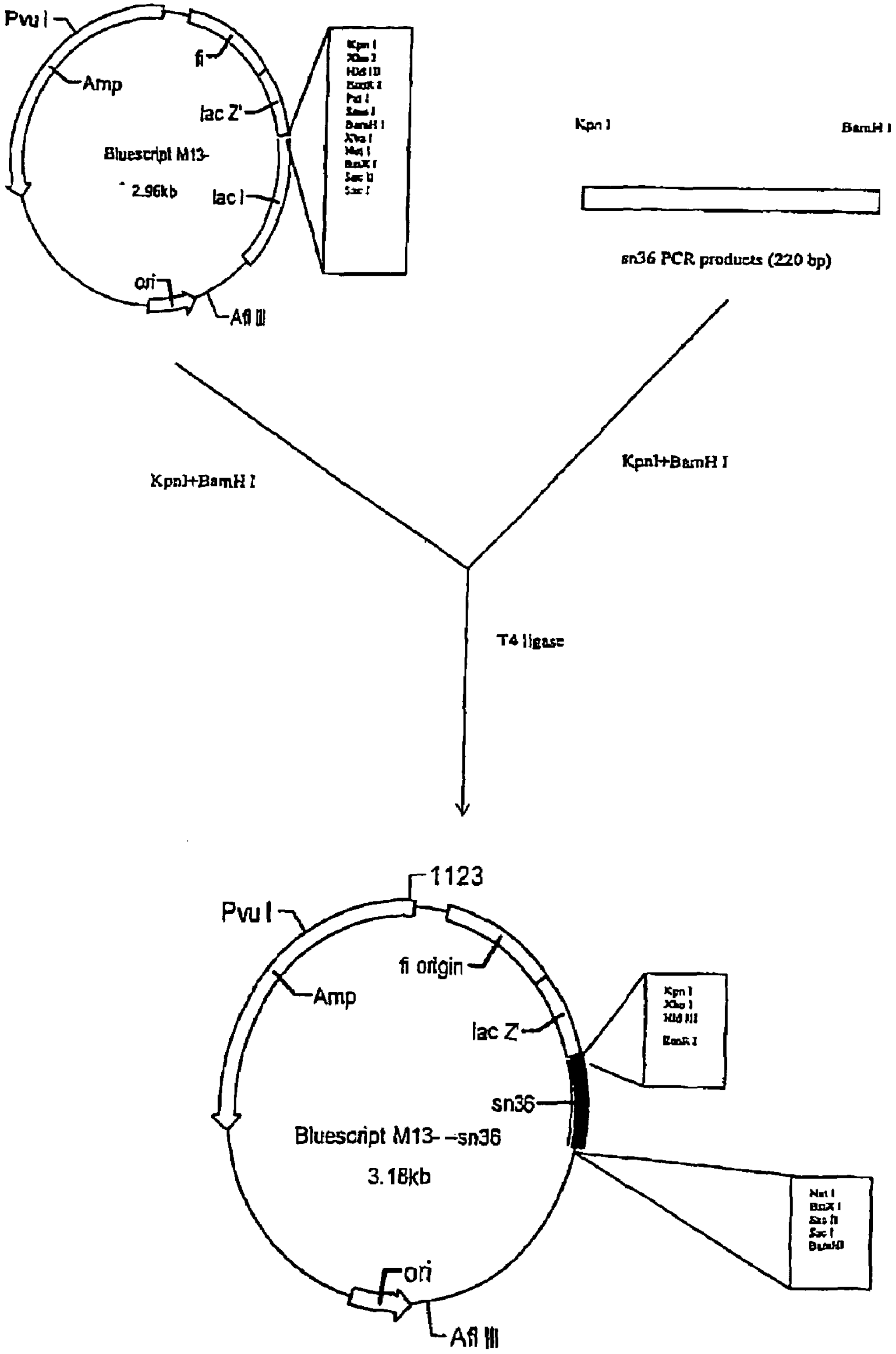

FIG. 5 The construction pattern of the recombinant plasmid pBSK-sn36 containing sn36 gene.

Figure 6:
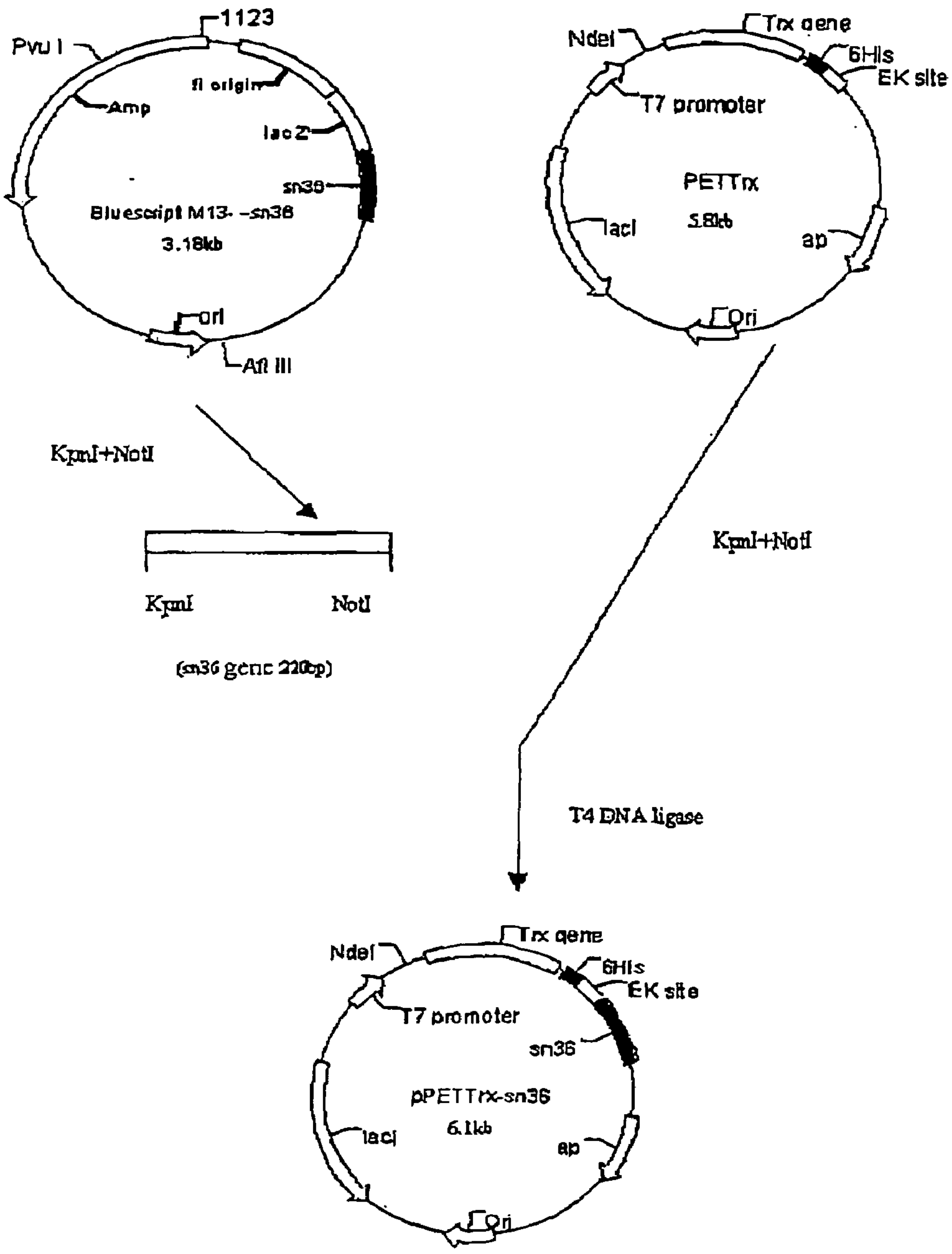

FIG. 6 The construction pattern of the recombinant plasmid pPETTrX-sn36 containing sn36 gene.

Figure 7:
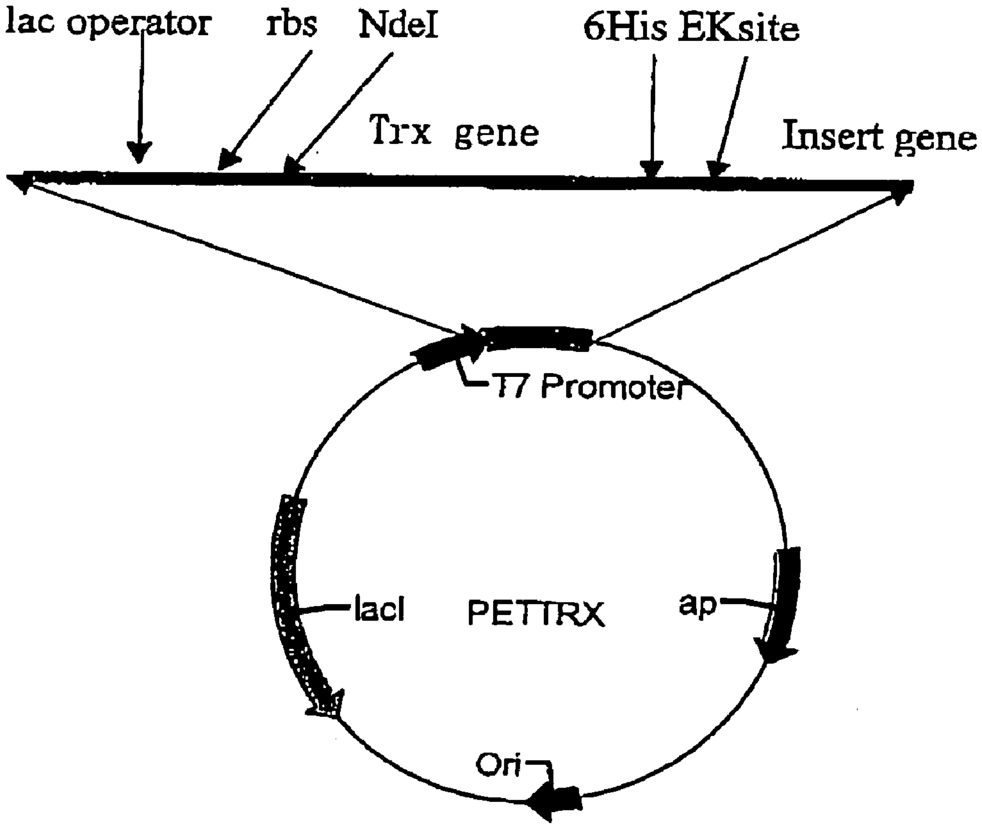

FIG. 7 Physical map of the soluble fusion protein expression vector PETTrX.

Figure 8:
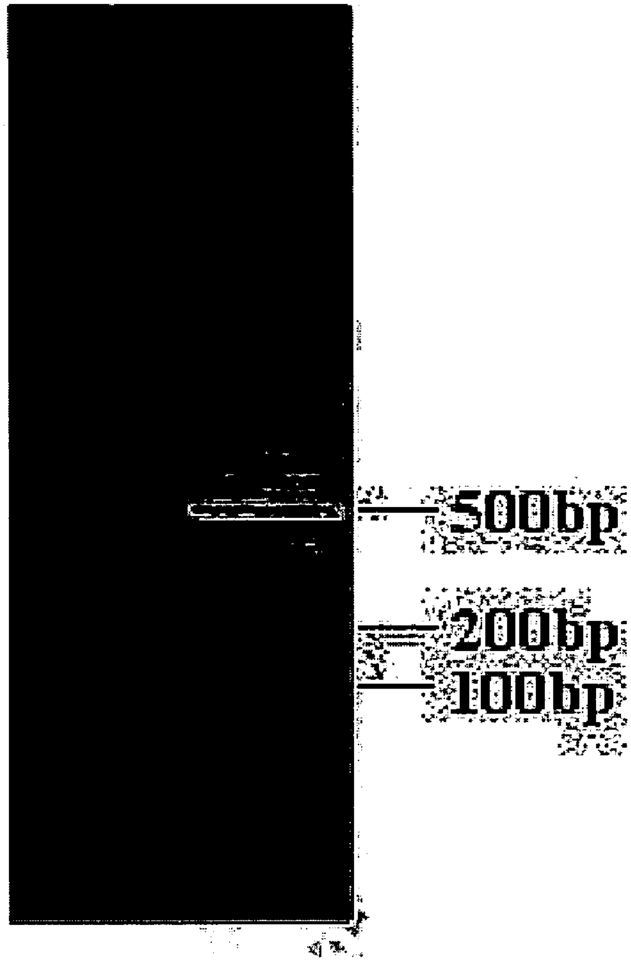

FIG. 8 Electrophoresis analysis of the PCR product of sn 36 of short chain neurotoxin gene from sea snake—*Lapemis hardwickii*. M. 100 bp DNA Ladder, 1. PCR product of sn36; 2. negative control of PCR reaction.

Figure 9:
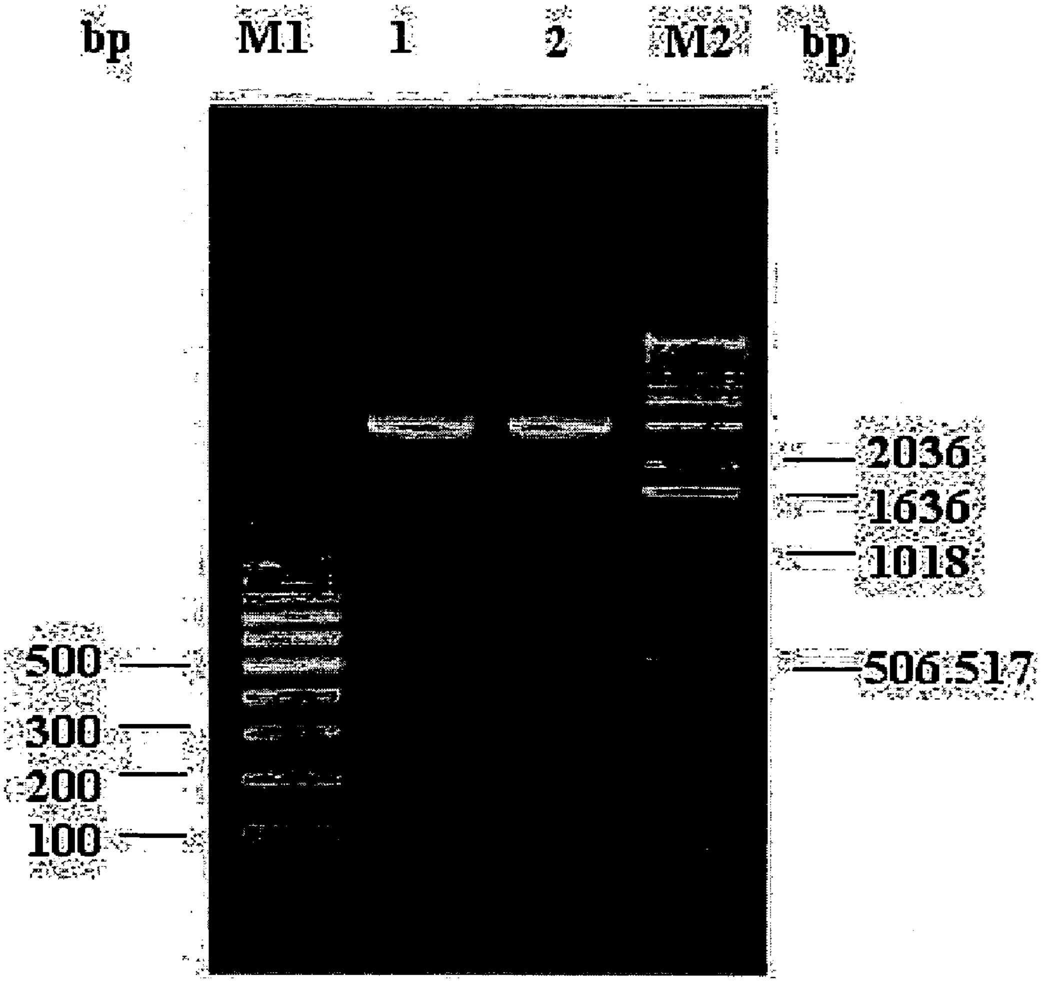

FIG. 9 Electrophoresis analysis of the recombinant plasmid pBSK-sn36 digested by restriction endonuclease. M1. 100 bp DNA Ladder, M2. 1 kb DNA Ladder, 1: pBSK-sn36 digested by KpnI and BamHI, 2. pBluescript M13(+) digested by KpnI and BamHI.

Figure 10:
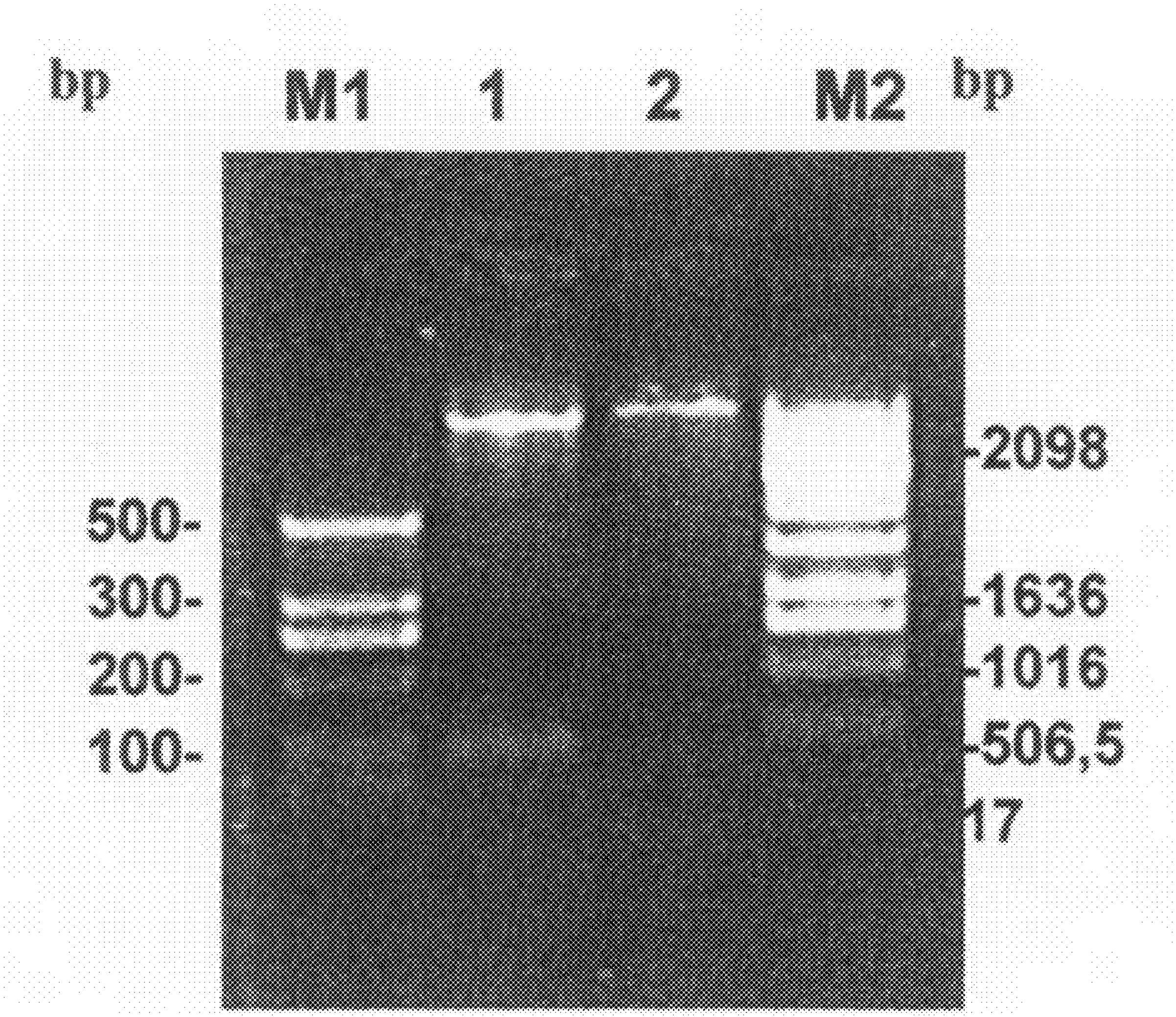

FIG. 10 Electrophoresis analysis of the recombinant plasmid pETTrX-sn36 digested by restriction endonuclease. M1. 100 bp DNA Ladder, M2. 1 kb DNA Ladder, 1. pETTrX-sn36 digested by KpnI and NotI, 2. pETTrX digested by KpnI and NotI.

Figure 11:
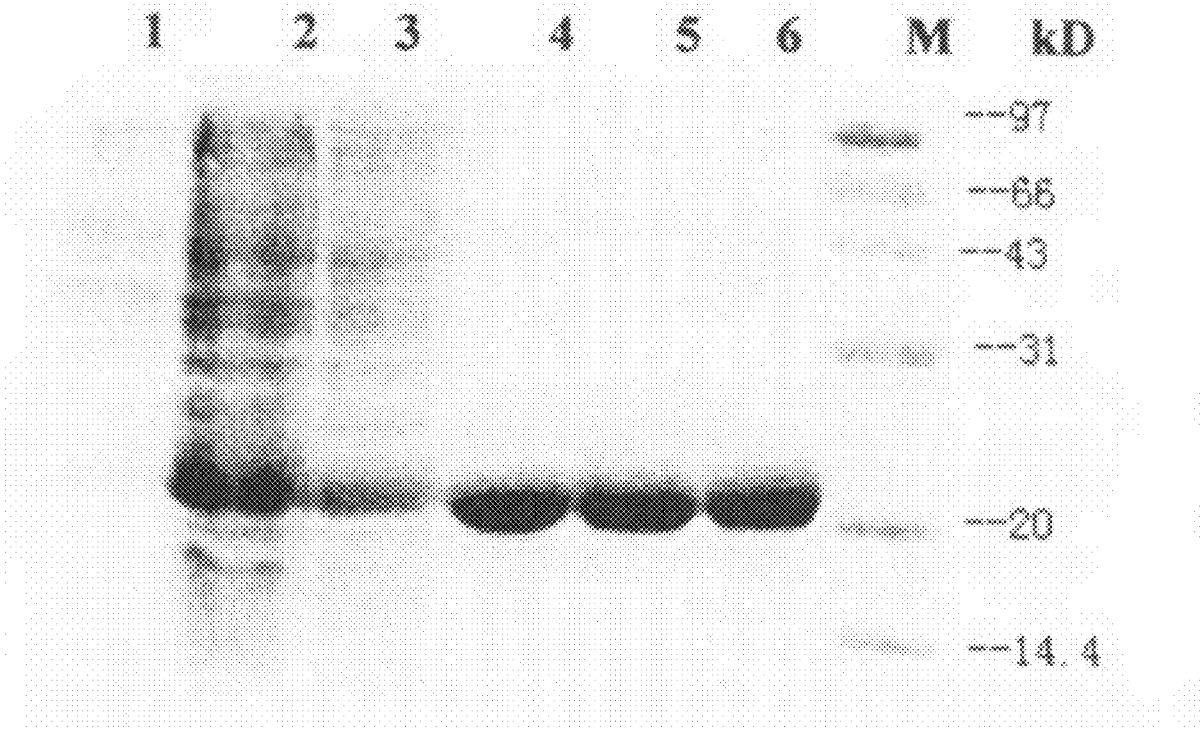

FIG. 11 The SDS-PAGE analysis of the recombinant neurotoxin protein SN12 of sea snake—*Lapemis hardwickii.* 1. Total bacteria proteins of strain BL21 (pET22b), 2. Total bacteria proteins of BL21 (pETTRXsn12), 3. Total soluble bacteria proteins of BL21 (pETTRXsn12), 4. recombinant fusion neurotoxin SN12 purified by $Ni^{2+}$ Chelating Sepharose, 5-6. recombinant fusion neurotoxin SN12 purified by Sephacryl S-100HR, M. Protein marker.

Figure 12:
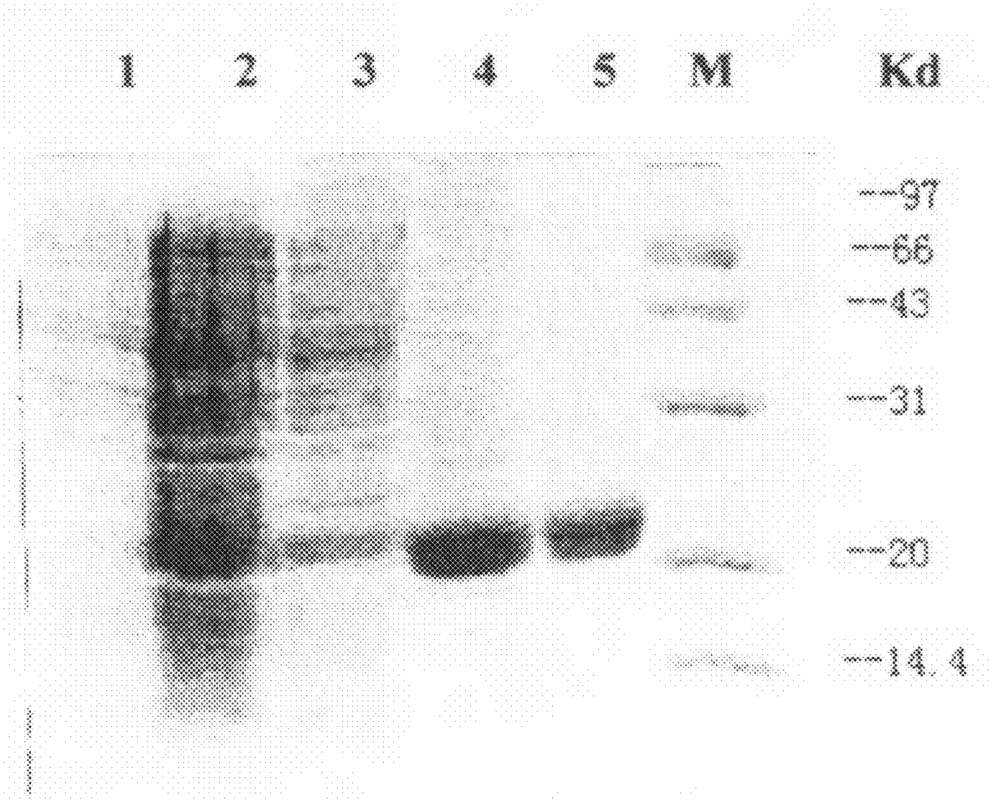

FIG. 12 The SDS-PAGE analysis of the expression of the recombinant neurotoxin protein SN36. 1 Total bacteria proteins of strain BL21 (pET22b), 2. Total bacteria proteins of BL21 (pETTRXsn36), 3. Total soluble bacteria proteins of BL21 (pETTRXsn36), 4. recombinant fusion neurotoxin SN36 purified by $Ni^{2+}$ Chelating Sepharose, 5. recombinant fusion neurotoxin SN36 purified by Sephacryl S-100HR, M. Protein marker.

Figure 13:
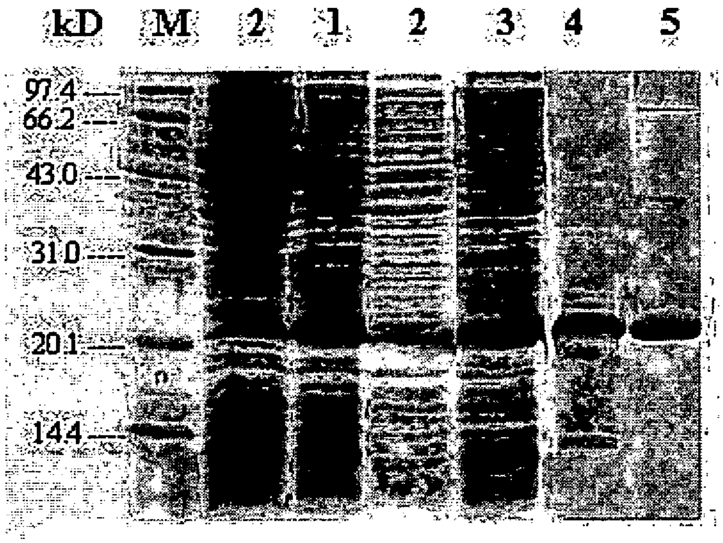

FIG. 13 The SDS-PAGE analysis of the expression of the recombinant neurotoxin protein SN160. 1. Total bacteria proteins of BL21 (pETTRXsn160), 2. Total bacteria proteins of strain BL21 (pET22b), 3. Total bacteria proteins of BL21 (pETTRXsn160), 4. recombinant fusion neurotoxin SN160 purified by $Ni^{2+}$ Chelating Sepharose, 5. recombinant fusion neurotoxin SN160 purified by Sephacryl S-100HR, M. Protein marker.

Figure 14:
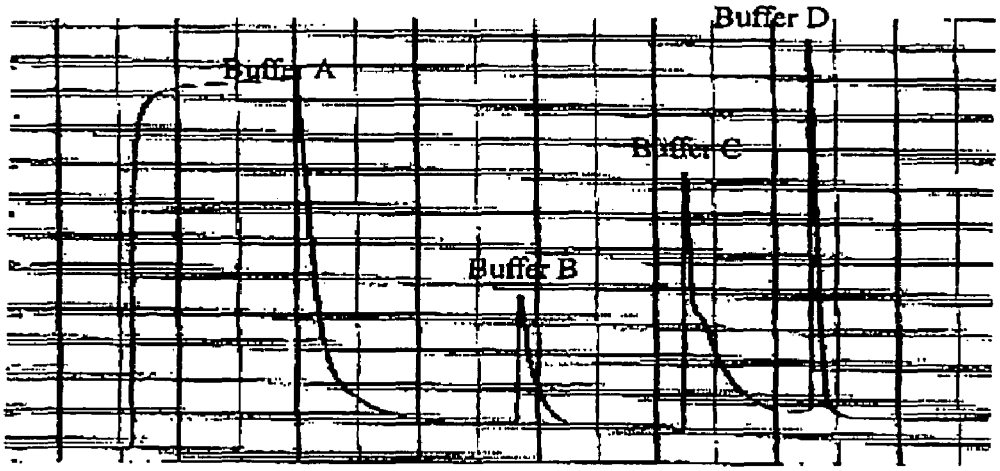

FIG. 14 $Ni^{2+}$ Chelating Sepharose affinity chromatography map of the recombinant neurotoxins.

Figure 15:
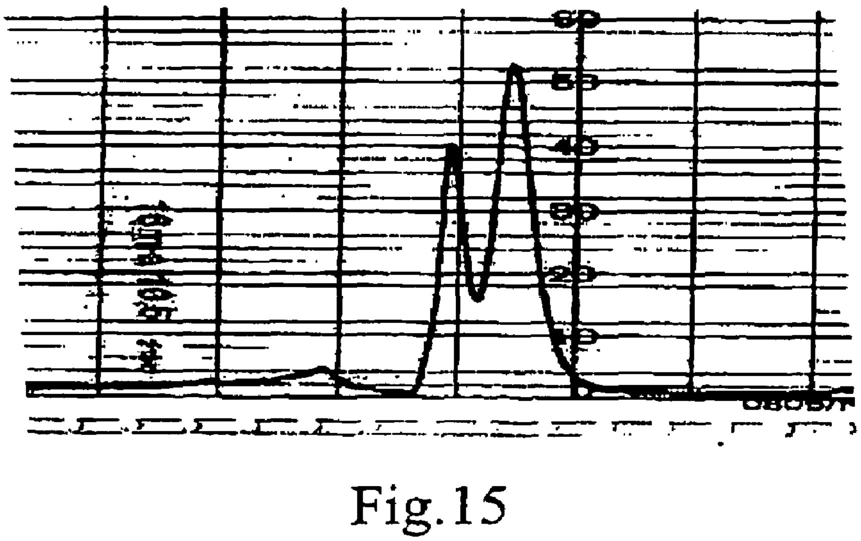

FIG. 15 Sephacryl S-100HR gel filtration chromatography of the recombinant neurotoxins.

DETAILED DESCRIPTION OF THE INVENTION

The purpose of this invention is to obtain cDNA clones encoding sea snake neurotoxin by constructing cDNA library of sea snake toxin from *Lapemis hardwickii*, and express isolated neurotoxin protein of sea snake having bioactivity using highly efficient expression system of *E. coli* for further functional research and drug development.

The snake we chose in this invention belongs to a sea snake family, *Lapemis hardwichii* genus, named Hydrophiinae *Lapemis Hardwickii* Gray, it was collected from Beihai City, Guangxi Province. The construction of the cDNA library of the venom from *Lapemis hardwickii* was carried out as follows: first, the sea snake crude venom glands were obtained by dissecting, then total RNA were extracted, mRNA were isolated and used as templates for reverse transcription to obtain full length cDNA, next cDNA were ligated into plasmid vector pcDNA3.0, plasmids were transformed into *E. coli*, finally the cDNA library of the toxin from *Lapemis hardwickii* were successfully constructed.

This invention reports three cDNA clones that encoding short chain neurotoxin of sea snake—*Lapemis hardwickii* were found by large scale sequencing the cDNA library of toxin of sea snake—*Lapemis hardwickii*, named sn12, sn36 and sn160 respectively. All of them encode 81 amino acids residues including a signal peptide of 21 amino acids and a mature peptide of 60 amino acids, p1 values are all about 8.7, molecular weights are approximately 9000 dalton, they all share the same typical characteristic of primary structure of short chain neurotoxin, with the only variance being one amino acid located at the $46^{th}$ of the mature peptide, which is $Pro^{46}$, $His^{46}$ and $Arg^{46}$, respectively. The nucleotide sequence thereof was shown in SEQ ID No. 1 and the amino acid sequence thereof was shown in SEQ ID NO.2.

A pair of universal primers (SEQ ID NO. 3 and SEQ ID NO. 4) were designed in this invention, three genes encoding the mature peptides of short chain neurotoxin from sea snake—*Lapemis hardwickii* were then obtained by PCR amplifying using designed primers, the PCR products were cloned into prokaryotic fusion expression vector pETTRX, thus three expression plasmids pETTRXsn12, pETTRXsn36, pETTRXsn160 were constructed. Studies were performed to find the optimum cultivation time, induction time and temperature, under optimum conditions, the expressed fusion proteins SN12, SN36, and SN160 could constitute beyond 17% of the total bacterial proteins, almost all are soluble proteins.

In this invention, studies on the optimum purification conditions of the recombinant fusion proteins SN12, SN36, and SN160 were also carried out, $Ni^{2+}$ Chelating Sepharose Affinity Chromatography followed by Sephacryl S-100HR gel chromatography was used to purify the recombinant fusion proteins, the purity of the recombinant neurotoxins was up to 98%.

The purified neurotoxins mentioned in this invention could be used in clinic treatments by intramuscular injection and intravenous injection, sample injected was $\frac{1}{2500}^{th}$ of $LD_{50}$ of mice {one dosage each day, 1~2 bottle each time, for particular two dosages each day and 1 bottle each time. As for acute pain, withdrawal on abolition of pain. As for chronic pain, 3~5 more administrations for consolidation. 20 days for one period of treatment and repetitive periods are needed if necessary The recombinant short chain neurotoxin proteins of sea snake—*Lapemis hardwickii* obtained in this invention was bioactive. These recombinant neurotoxins purified by applying to Sephacryl S-100HR gel chromatography were injected into NIH mice by intraperitoneal injection, respectively, positive neurotoxin activity were shown after injection, the $LD_{50}$ of these purified fusion proteins SN12, SN36 and SN160 were 1.734 mg/Kg, 2.544 mg/Kg and 6.557 mg/Kg respectively. According to the research reported by Fox, J. W (Fox, J. W., Elzinga, M. and Tu, A. T. Amino acid sequence of a snake neurotoxin from the venom of *Lapemis hardwickii* and the detection of a sulfhydryl group by laser Raman spectroscopy. FEBS Lett. 1977, 80(1): 217-220), the $LD_{50}$ of natural SN12 was 0.2 mg/kg, the neurotoxin activity of our recombinant proteins were only about 1/12 of the natural protein.

The recombinant short chain neurotoxin proteins of sea snake—*Lapemis hardwickii* mentioned in this invention had obvious analgesic effect on mice, pain threshold value of the mice that were injected with recombinant short chain neurotoxin proteins of sea snake—*Lapemis hardwickii* obviously rose. Among these recombinant proteins, SN160 had the best analgesic effect, the threshold value rose 63.1%. The recombinant short chain neurotoxin proteins of sea snake—*Lapemis hardwickii* of the invention could be used to develop the neotype sedative drug used for sedative, anesthesia and abstinence of drugs, or clinically myasthenia gravis diagnosis and the like.

A 220 bp fragment was obtained after the expression plasmid vector was digested by KpnI and NotI, this fragment encoded fusion protein of 6×His tag and the mature peptide of short chain neurotoxin of sea snake—*Lapemis hardwickii*, the other 5.9 kb fragment was the pETTRX vector DNA.

The replication of the expression plasmid vector was carried out by using methods recommended by Sambrook (Sambrook, et al. 1989, Molecular cloning. Cold Spring Harbor Laboratory Press. USA). $CaCl_2$ transformation method was used to transform plasmids into *E. coli* strain DH5α or BL21(DE3), then LB broth containing 100 μg/ml Ampicillin was used to select positive clones, plasmids DNA was extracted by routine method suggested by Sambrook.

Further illustration were carried out as follows by using examples.

EXAMPLE

Example 1

The Construction of cDNA Library of the Toxin from Sea Snake—*Lapemis hardwickii*

Total RNA was extracted from the homogenous venom gland tissues of sea snake—*Lapemis hardwickii* by using one-step-extraction methods with hot phenol according to <<Modern Molecular Biology Experiment technique>>[11]; mRNA was extracted later by using mRNA Purification Kit (Amersham Pharmacia); Then TimeSaver™ cDNA Synthesis Kit was used for the cDNA synthesis (Amersham Pharmacia), all protocol details were recommended by the manufacturer.

Total RNA of venom gland extracted by one-step with guanidine isothiocyanate was electrophoresed on 1% denaturing formaldehyde gel, three obvious rRNA bands—28S, 18S and 5.8S and several specific RNA bands were represented within smear RNA (as shown in FIG. 1), this indicated that total RNA was intact and the venom gland tissues were highly differentiation. mRNA extracted by using mRNA Purification Kit was electrophoresed as well, homogeneous smear was detected (as shown in FIG. 1), indicating the intactness of the mRNA. Then 5 μg mRNA was used for synthesis of double-strand cDNA by reverse transcription PCR. Electrophoresis analysis showed that synthesized cDNA were smear. Fragment sizes ranged from 200 bp to 8 kb, mainly within the region less than 2 kb, especially centralized near 500 bp (as shown in FIG. 2), these results indicated that most proteins encoded by synthesized cDNA were small, this matched with the fact that sea snake venom is rich in small molecular peptides[14]. Synthesized cDNA was inserted into plasmid vector pcDNA3.0 to construct the cDNA expression library, which totally comprised $9.96\times10^5$ clones. Plasmids from total library were isolated, restriction endonuclease and PCR analysis showed that the size of inserted cDNA ranged from 500 bp to 8 kb, two brighter bands of approximately 500 bp and 1 kb were especially presented (as shown in FIG. 3), several faint bands were also detected in other regions. Among all the clones, 172 clones were selected to isolate plasmids for restriction endonuclease analysis, the results showed that over 95% of the clones were recombinants, which indicated the high quality of the cDNA expression library.

Example 2

Sequencing and Analyzing of the Short Chain Neurotoxins of Sea Snake—*Lapemis hardwickii*

About 500 cDNA clones were randomly selected to isolate plasmid DNA by PEG purification[13]. DNA sequencing was performed using ABI 377 DNA Sequencer (available from BAO biological engineering Inc. DaLian) with universal T7 and Sp6 primers, each clone was sequenced positively and reversely to ensure the accuracy of gene sequence. The results showed that the abundance of the neurotoxin genes from cDNA expression library of sea snake—*Lapemis hardwickii* was very high. Among these neurotoxins sequenced, there are three different genes named sn12, sn36 and sn160 respectively encoding a protein of 81 amino acids, wherein a signal peptide of 21 amino acids and a mature peptide of 60 amino acids, all of them share the same typical primary structure of short chain neurotoxin, with the only variance of one amino acid, which locates at the $46^{th}$ of the mature peptide, and it is $Pro^{46}$, $His^{46}$ and $Arg^{46}$ respectively.

Searching for the homology of these three neurotoxins in the protein database were performed using the program BLASTTP, the results showed that the amino acid sequence of mature peptide of short chain neurotoxin encoded by sn12 was as same as the short chain neurotoxin that were isolated and purified from toxin of sea snake—*Lepamis hardwickii* by Tu, et al., [1], while the proteins encoded by sn36 and sn160 were found to be new short chain neurotoxins. In addition, none of the same nucleotide sequences were found in Genbank so far.

The nucleotide sequences of sn12 (SEQ ID NO. 5), sn36 (SEQ ID. NO. 6), and sn160 (SEQ ID NO. 7) and predicted amino acid sequences of sn12 (SEQ ID NO. 8), sn36 (SEQ ID NO. 9) and sn160 (SEQ ID NO.10) were shown in FIG. 4. More than three different cDNA clones of the same gene were sequenced to ensure the accuracy of gene sequence, considering possible error introduced by cDNA synthesis and DNA sequencing. Sequences analysis in FIG. 4 showed that even nonencoding nucleotide sequence of the three genes of sn12, sn36 and sn160 were also highly homogenous, which is similar to the research reported by Tamiya et. al., (1999)[3].

Example 3

The Construction of Recombinant Sea Snake—*Lapemis hardwickii* Short Chain Neurotoxin Expression Plasmid A pair of primers were designed according to the 3' and 5' sequence of the sn12, sn36 and sn160 genes that encoding the mature peptide, the forward primer (SEQ ID NO. 3) was:

```
5'-CGG GGT ACC GAC GAC GAC GAT AAA
       Kpnl  recognition site for enterokinase
   ATG ACA TGT TGC AAC CAA CAG TC-3'
```

the reverse primer (SEQ ID NO. 4) was:

```
5'-CGC GGA TCC TTA ATT GTT GCA TTC GTT
       BamHI
TGT ATG GC-3'
```

PCR amplification and gene clone were performed using routine methods [13]. The details of expression plasmid construction procedure were shown in FIGS. 5 and 6.

The genes were then inserted into the prokaryotic fusion expression vector pETTRX which was previously constructed by our lab, then three expression plasmid pETTRXsn12, pETTRXsn36, pETTRXsn160 were obtained. The PCR products were approximately 220 bp (as shown in FIG. 7), encoding 60 amino acid residues. The target genes were identified to be correctly inserted into the vector by endonuclease digestion and DNA sequencing.

The expression vector pETTRX contains a T7 promoter, it uses molecular chaperone TRX as a fusion chaperone, which helps recombinant protein correctly folding and expresses as a soluble protein. The C terminal of TRX has a hinge region and a 6×HIS structure which make it easy to purify the proteins by using the immobilized metal ligand chelating chromatography. The forward primer contains a recognition site for enterokinase, which helps to obtain foreign protein monomer. The structure of the vector pETTRX is shown in FIG. 8.

Example 4

The Expression of Recombinant Short Chain Neurotoxin Fusion Protein of Sea Snake—*Lapemis hardwickii*

Plasmids pETTRXsn12, pETTRXsn36 and pETTRXsn160 were transformed into *E. coli* strain BL21 (DE3). After induction, the lysate of gene engineering bacteria lysed by sonication were then subjected to SDS-PAGE analysis, the results indicated that gene engineering bacteria did express an obvious distinctive foreign protein after induction. The expressed foreign protein had the molecular weight of approximately 22.1 kD, which matched with the predicted size of the proteins with PROTEIN ANALYSIS software.

Based on the experiment results, though more recombinant proteins were expressed when bacteria were induced by high temperature, less were expressed when bacteria were induced by low temperature, the recombinant proteins induced by low temperature were better folded, which might enhance the solubility of the recombinant proteins, then relatively speaking, the bioactivity of the recombinant proteins would be higher. After some groping studies on cultivation conditions such as incubation time, induction time and temperature, the optimum cultivation conditions were: one single colony bacteria were grown at 37° C., 250 rpm overnight in 50 ml LB broth having ampicillin-resistance, then 20 ml of the culture were used to cultivate in 2L LB broth having ampicillin-resistance at 37° C., 250 rpm up to $OD_{600=0.6}$, the bacteria were then induced at 26° C., 250 rpm for 10 hours by adding 100 mM IPTG and 20% glucose to a final concentration of 1 mM and 0.2% (v/v), and then centrifuged to obtain the bacteria. The thin-layer chromatogram scanning analysis indicated that under these conditions the expressed fusion protein SN12, SN36 and SN160 could constitute beyond 17% of the total bacteria proteins, and almost all were soluble proteins.

Example 5

The Purification of the Recombinant Short Chain Neurotoxin Fusion Protein of Sea Snake—*Lapemis hardwickii*

Since the amino acid sequences of the three recombinant neurotoxins were highly similar to each other with the only variance of the $46^{th}$ residue, same procedure was used to purify three fusion proteins.

Total bacteria were collected and resuspended, then lysed by sonication, the supernatant fluid was applied to a $Ni^{2+}$ chelating sepharose affinity chromatography to purify the fusion protein, Sephacryl S-100HR gel chromatography was used for the further purification, SDS-PAGE analysis and thin-layer scanning analysis indicated that the purity of all the recombinant neurotoxins was up to 70% and 98% (as shown in FIG. 9, FIG. 10, FIG. 11). As a result, 2 L LB broth was used to cultivate the gene engineering bacteria, approximately 100 mg purified fusion proteins were ultimately obtained.

In order to increase the yield and the concentration of the recombinant proteins, simplify the experiment procedures and shorten the protein treatment time, when using $Ni^{2+}$ chelating sepharose affinity chromatography to purify the recombinant proteins, we did not use strict elution conditions. Based on the fact that the foreign proteins expressed by vector plasmid pETTRX could strongly combine with the $Ni^{2+}$ chelating sepharose affinity chromatography column, we used simpler elution conditions: 50 mM PBS, 500 mM NaCl, pH7.8 (buffer A); 50 mM PBS, 500 mM NaCl, 6.0 (buffer B); 150 mM imidazole, 50 mM PBS, 500 mM NaCl, pH6.0 (buffer C), 400 mM imidazole, 50 mM PBS, 500 mM NaCl, pH6.0 (buffer D). Recombinant neurotoxin proteins were obtained when eluted with buffer D (as shown in FIG. 12). Then the initially purified recombinant proteins by $Ni^{2+}$ chelating sepharose affinity chromatography column were applied to Sephacryl S-100HR gel chromatography for further purification, using physiological saline as elution buffer, fraction collector were used to collect the eluted proteins according to the elution peak (as shown in FIG. 13), and SDS-PAGE analysis was used to estimate the protein eluted with best separate effect. Gel filtration chromatography were performed for further purification and desalting, and the purified proteins eluted with physiological saline could be used straightly to perform bioactivity test avoiding dialysis.

Example 6

Neurotoxicity Identification of the Recombinant Short Chain Neurotoxin Fusion Protein of Sea Snake—*Lapemis hardwickii*

100 NIH mice weighing 19~21 g were divided into 5 groups, 20 mice for every group with half-and-half male and female animals. The recombinant short chain neurotoxins, sterilized by filtration, were injected abdominally to all of the mice at 5 suitable concentrations respectively. The chaperone TRX expressed by pETTrx expression vector and purified under the same conditions, was taken as negative control. Observe the responses of mice and record the amount of death in every group. Take advantage of linear regress software of Microsoft Excel and draw straight lines according to logarithm dosage and experience probability unit and at last calculate $LD_{50}$.

All of the NIH mice, subjected to abdominal injection of the three recombinant neurotoxins purified through gel filtration chromatography, exhibited typical neurotoxic symptom such as pilo-erection, sluggishness, twitching, abolition of righting reflex, dyspnea, malfunction of excretory system and like, intense tic and asphyxial death ultimately. Heartbeat was observed within ten minutes after death. At the same time, as to the negative control with fusion chaperone TRX dissolved in physiological saline, no neurotoxic symptom could be seen. It is evident that three recombinant neurotoxins exhibit neurotoxicity in a fusion. Though only one residue difference in amino acid sequences of three recombinant neurotoxins, they display different potency of neurotoxicity. The most potent is SN160, followed by SN12, and the least is SN36.

After neurotoxicity of recombinant neurotoxins were identified, we set out to make quantitative estimation of their neurotoxicity in terms of $LD_{50}$ as an index. Preliminary tests were carried out in several sections, so as to decide 5 injection dosages of three toxins to calculate medial lethal concentration. 100 NIH mice were randomly divided into 5 groups, 20 mice every group with half-and-half male and female animals and were abdominally injected with 0.5 ml of the recombinant neurotoxin at different concentration respectively. Taking dosage logarithm as abscissa and experience probability unit as ordinate, we calculated $LD_{50}$ by deduce the dosage logarithm corresponding to probability unit of 5. Particular experiment data are shown in table 1.

TABLE 1

$LD_{50}$ value of recombinant short chain neurotoxins SN12, SN36 and SN160 on NIH mice

| | Injection dose mg/kg group | | | | | linear regress | $LD_{50}$ |
|---|---|---|---|---|---|---|---|
| | 1 | 2 | 3 | 4 | 5 | equation | (mg/kg) |
| Recombinant neurotoxin SN160 | 2.20 | 1.999 | 1.816 | 1.650 | 1.500 | y = 8.395x + 2.9916 | 1.734 |
| Death number of NIH mice | 16 | 14 | 12 | 8 | 6 | | |
| Recombinant neurotoxin SN12 | 2.917 | 2.723 | 2.544 | 2.399 | 2.155 | Y = 9.0673x + 1.3225 | 2.544 |
| Death number of NIH mice | 14 | 12 | 10 | 7 | 4 | | |
| Recombinant neurotoxin SN36 | 8.50 | 7.44 | 6.52 | 5.71 | 5.00 | Y = 5.5887x + 0.4358 | 6.557 |
| Death number of NIH mice | 14 | 12 | 12 | 6 | 4 | | |

Example 7

Analgesia of the Recombinant Short Chain Neurotoxin Fusion Proteins of Sea Snake—*Lapemis hardwickii*

Hot plate method was employed to study analgesia according to experimental method of pharmacology. Mice were put onto metal plates preheated to 55° C. Frequency of licking hindfoot was recorded as an index of pain response. Mice of dullness or with allergy were eliminated before the experiment.

150 female mice weighing 18.about.22.5 g were randomly divided into control group and administration groups. The administration groups were subjected to abdominal injection with ⅛ $LD_{50}$, ¼ $LD_{50}$, ½ $LD_{50}$ respectively while the control group with 0.2 ml of physiological saline.

As shown from Table 2, analgesia effect got intensive with dosage increased. The three short chain neurotoxins exhibited discriminating effect of analgesia. The most potent is SN106 followed by SN12, and the least is SN36.

TABLE 2

The analgesia effect of the recombinant short chain neurotoxins of sea snake-*Lapemis hardwickii* (Hot plate method)

| | | | latent period (X ± SD) | | percent of |
|---|---|---|---|---|---|
| batch | dosage | number of examples | before admin-istration | after adminisatration | pain threshold rises (%) |
| 1 | ½ $LD_{50}$ SN12 | 20 | 17.1 ± 5.7 | 25.9 ± 5.4 | 51.3 |
| | ½ $LD_{50}$ SN36 | 20 | 16.5 ± 3.5 | 23.9 ± 6.3 | 44.8 |
| | ½ $LD_{50}$ SN160 | 20 | 17.6 ± 4.4 | 28.7 ± 3.5 | 63.1 |

TABLE 2-continued

The analgesia effect of the recombinant short chain neurotoxins of sea snake-*Lapemis hardwickii* (Hot plate method)

| batch | dosage | number of examples | latent period (X ± SD) before admin-istration | latent period (X ± SD) after adminisatration | percent of pain threshold rises (%) |
|---|---|---|---|---|---|
| 2 | ¼ $LD_{50}$ SN12 | 20 | 18.6 ± 5.4 | 27.1 ± 5.9 | 45.7 |
| | ¼ $LD_{50}$ SN36 | 20 | 17.2 ± 4.1 | 23.6 ± 3.5 | 37.2 |
| | ¼ $LD_{50}$ SN160 | 20 | 17.5 ± 4.4 | 27.5 ± 7.5 | 57.1 |
| 3 | ⅛ $LD_{50}$ SN12 | 20 | 18.0 ± 3.8 | 24.6 ± 3.5 | 36.7 |
| | ⅛ $LD_{50}$ SN36 | 20 | 16.6 ± 4.8 | 20.0 ± 3.5 | 20.5 |
| | ⅛ $LD_{50}$ SN160 | 20 | 17.2 ± 4.1 | 24.9 ± 3.5 | 44.7 |
| 4 | Negative control | 20 | 18.1 ± 4.0 | 19.4 ± 4.6 | 7.1 |

The invention claimed is:

1. A recombinant neurotoxin from sea snake *Lapemis hardwickii* comprising the amino acid sequence shown in SEQ ID NO:2, wherein “Xaa” at position 46 does not represent Proline.

2. The recombinant neurotoxin of claim 1, wherein said neurotoxin is encoded by the nucleotide sequence set forth in SEQ ID NO:1.

* * * * *